(12) United States Patent
Scheffer (10) Patent No.: US 10,422,366 B2
(45) Date of Patent: Sep. 24, 2019

(54) MEDICAL DRAINAGE TUBE ANCHOR

(71) Applicant: William L. Scheffer, Cardington, OH (US)

(72) Inventor: William L. Scheffer, Cardington, OH (US)

( * ) Notice: Subject to any disclaimer, the term of this patent is extended or adjusted under 35 U.S.C. 154(b) by 0 days.

(21) Appl. No.: 15/987,343

(22) Filed: May 23, 2018

(65) Prior Publication Data

US 2019/0101144 A1  Apr. 4, 2019

Related U.S. Application Data

(60) Provisional application No. 62/567,773, filed on Oct. 4, 2017.

(51) Int. Cl.
*F16B 2/24* (2006.01)
*A61M 1/28* (2006.01)
*E03D 9/00* (2006.01)
*A61J 1/10* (2006.01)
*A61M 39/08* (2006.01)

(52) U.S. Cl.
CPC .............. *F16B 2/248* (2013.01); *A61J 1/10* (2013.01); *A61M 1/285* (2013.01); *A61M 39/08* (2013.01); *E03D 9/00* (2013.01); *A61M 2209/082* (2013.01)

(58) Field of Classification Search
CPC ... F16B 2/248; A61J 1/10; E03D 9/00; A61M 1/285; A61M 2209/082

USPC .......... 248/465.1, 107, 112, 153, 175, 218.1, 248/249, 302, 75; 211/41.4, 85.31, 90.03, 211/106, 112, 119, 126.8, 126.9, 133.2, 211/133.5, 181.1; 4/223, 420.3
See application file for complete search history.

(56) References Cited

U.S. PATENT DOCUMENTS

| | | | | |
|---|---|---|---|---|
| 3,669,394 A | * | 6/1972 | Loucks ................... | E04F 21/05 248/218.4 |
| 3,800,365 A | * | 4/1974 | Bruggert ................. | F16B 2/248 47/47 |
| 4,809,941 A | * | 3/1989 | Sheridan ............... | A47B 96/061 248/235 |
| 5,788,403 A | * | 8/1998 | Dison ..................... | E04B 1/944 248/228.7 |
| 2002/0000504 A1 | * | 1/2002 | Bayne ................... | F21V 21/088 248/302 |
| 2016/0068096 A1 | * | 3/2016 | Hood ........................ | B60P 7/08 24/302 |

* cited by examiner

*Primary Examiner* — Muhammad Ijaz
(74) *Attorney, Agent, or Firm* — Miracle IP; Bryce D. Miracle (57) ABSTRACT

In accordance with the present application, an anchor device is provided which is configured to secure a drainage tube having nozzle end to a waste receptacle. In the version, the anchor device generally comprises an attachment rim assembly positionable for supporting the anchor device to the rim of the waste receptacle and a suspension arm operably attached to the attachment rim assembly for suspending the discharge nozzle end of the drainage tube towards the center of the waste receptacle.

20 Claims, 8 Drawing Sheets

MEDICAL DRAINAGE TUBE ANCHOR

CROSS-REFERENCE TO RELATED APPLICATIONS

This application is a U.S. Non-Provisional patent application which claims priority to U.S. Provisional Patent Application No. 62/567,773, filed Oct. 4, 2017 and titled "MEDICAL DRAIN LINE ANCHOR," which is hereby incorporated by reference in its entirety.

FIELD OF THE INVENTION

The present invention relates to the field of medical devices, and more specifically, to an accessory for a medical treatment apparatus, such as for instance, a dialysis machine, and more particularly to a support assembly configured to attach a drainage tube to a standard commode or toilet to promote the drainage of fluids from a waste side of a dialysis machine in an efficient, secure and sanitary manner.

BACKGROUND

The kidneys perform one of the most important functions in the elimination of waste in a human body; they filter extra water and waste, thereby cleaning the blood and facilitating production of an adequate level of red blood cells. When the kidneys fail, the fluids are retained in the blood and do not circulate properly throughout the body. Thus, waste material builds up in the body seriously endangering health and wellbeing of the person.

Dialysis imitates the work of a kidney. Technology has developed two types of dialysis treatment: hemodialysis and peritoneal dialysis. The majority of the patients receive hemodialysis, by which the blood is circulated outside the body and cleaned inside the machine before returning to the patient. The patient's blood is drained into the dialysis machine, and a fluid called dialysate is then circulated through the machine. A thin, semi-permeable membrane separates the part that circulates the blood and the second part for the dialysate. As dialysate processes on one side of the membrane, and blood on the other, particles in waste from the bloodstream pass through the microscopic holes formed in the membrane and are washed away in the dialysate. Blood cells being too large to go through the membrane holes are returned to the body.

The other type of treatment, peritoneal dialysis, uses the patient's peritoneal membrane as a filter. The peritoneal membrane is a sack around the abdominal organs. This membrane is semi-permeable allowing water and toxic waste particles to pass through it but preventing larger blood cells to penetrate the membrane. In this type of treatment, a patient has a plastic tube catheter surgically implanted into the abdominal Wall. The patient or the patient's caregiver connects the patient's catheter tube; either to a machine that pumps dialysate fluid or the dialysate fluid is gravity fed by means of suspending a bag of dialysate fluid above the grade of the patient's catheter exit site, which slowly empties the dialysate fluid into the peritoneal cavity where it resides for a pre-determined period of time. During this dwell time the dialysate fluid absorbs the patient's excess water and toxic waste particles through the peritoneal membrane. The dialysate fluid containing the patients excess water and toxic waste is either extracted from the patient's peritoneal cavity by means of either a machine that pumps the waste material to a catch basin or a collection bag or is extracted from the patient by gravity which a collection bag that is placed below grade of the patient's catheter exit site. Similar to the hemodialysis method, the waste particles are removed with the dialysate and are discarded.

The peritoneal dialysis method has distinct advantages as it allows to significantly reduce the time needed for the dialysate to clean the blood and remove the waste. Additionally, the patient can perform the procedure in a non-hospital setting or at thousands of locations around the world. Such type of treatment may be administered by a caregiver that may not be very experienced in other types of the dialysis procedure.

Rather than performing manual peritoneal dialysis exchanges several times throughout the day, a patient can do automated peritoneal dialysis while they sleep. Automated peritoneal dialysis is done using a machine that fills the peritoneal cavity with fresh dialysis solution, also called PD fluid or PD solution, and after a specified dwell time, drains the solution with waste out of the body and then fills the peritoneal cavity with new dialysis solution. The average treatment time for automated peritoneal dialysis is 9 hours at night while the patient sleep.

When the patient performs the dialysis treatment by way of either the manual process CAPD or by use of a machine or cycler CCPD, the waste is drained into a bag or other container, which can then be emptied into a waste receptacle, such as a sink or a toilet by way of a drainage tube leading from the patient to the toilet. Often, the drainage tube end is haphazardly and loosely attached to the waste receptacle by way of an adhesive tape or other configuration. Thus, presenting an inherent risk that the drainage tube will be accidentally detached from the waste receptacle (person tripping over tube)—allowing the contents thereof including toxins to easily contaminate the surrounding area. Unfortunately for the caregiver and the patient, this can be dreadful to properly clean up and reattach the drainage tube to the waster receptacle in order to finish the dialysis process.

For the foregoing reasons, there is an extraordinary need for an improved apparatus which provides a secure drain line anchor and attachment to a waste receptacle such as a toilet, providing peace of mind throughout the already uncomfortably process of dialysis.

SUMMARY

In accordance with the present application, an anchor device is provided which is configured to secure a drainage tube having nozzle end to a waste receptacle. In an example embodiment, the anchor device is adapted to attach to a peripheral rim of the receptacle. The rim generally has a top surface of predetermined width, an interior surface of a predetermined depth terminating at a lower edge, and an exterior surface. In the version, the anchor device generally comprises an attachment rim assembly positionable for supporting the anchor device to the rim and a suspension arm operably attached to the attachment rim assembly for suspending the discharge nozzle end of the drainage tube towards the center of the receptacle. Generally, the anchor device is configured to collapse or clinch onto the peripheral rim while directional tension or pull is applied to the drainage tube, thereby securing the drainage tube nozzle end to the waster receptacle.

In a certain version of the application, the attachment rim assembly includes a first side frame structure or cradle configured to couple with the rim; a second side frame structure or cradle configured to couple with the rim; and a retaining bar which laterally extends between and connects the first and second side frame structures, the retaining bar is operably positioned below the top surface of the rim, and configured to retain a segment of the drainage tube between the waste receptacle exterior surface and the retaining bar.

In a certain version of the application, the suspension arm has a proximal end, a distal end, and a tube receiver positioned at the distal end. The suspension arm is operably attached to the attachment rim assembly, wherein the proximal end is operably positioned below the elevation of the lower edge of the peripheral rim interior surface, and wherein the tube receiver is operably configured to receive and secure the drainage tube near the discharge nozzle end.

In other certain versions, at least one of the first side frame structure and the second side frame structure comprise a top member which extends the width of the top surface, an interior member which extends downward adjacent the interior surface of the rim, and an exterior member which extends downward adjacent the exterior surface of the rim. In combination, the top member, interior member, and the exterior member form a generally rectangular profile with an open bottom for clamping over the cross-sectional profile of the peripheral rim of the waste receptacle.

In an embodiment, the anchor device may further include a securing member which operably connects the proximal end of the suspension arm with attachment rim assembly and positions the proximal end of the suspension arm below and under the rim of the waste receptacle.

In yet another version, the tube receiver provides a laterally extending tapered channel which is adapted to receive and retain the drainage tube near the discharge nozzle end without inhibiting drainage flow of waste material from the drainage tube.

In a version of the application, the retaining bar further comprises a channel guide which is configured to centrally retain a segment of the drainage tube between the waste receptacle exterior and the retaining bar.

In a preferred version of the application, the anchor device is formed by a singular unitary length of wire.

These and other features of the present invention will become readily apparent upon further review of the following specification and drawings.

BRIEF DESCRIPTION OF THE DRAWINGS

These and other features, aspects, and advantages of the present invention will become better understood with regard to the following description and accompanying figures where.

DETAILED DESCRIPTION

In the following description, for purposes of explanation and not limitation, specific details are set forth such as particular architectures, interfaces, techniques, etc. in order to provide a thorough understanding of the present invention. However, it will be apparent to those skilled in the art that the present invention may be practiced in other versions that depart from these specific details. In other instances, detailed descriptions of well-known devices and methods are omitted so as not to obscure the description of the present invention with unnecessary detail.

The following detailed description is of the best currently contemplated modes of carrying out exemplary versions of the invention. The description is not to be taken in the limiting sense but is made merely for the purpose illustrating the general principles of the invention, since the scope of the invention is best defined by the appended claims. Various inventive features are described below that can each be used independently of one another or in combination with other features.

Referring now to the figures wherein the showings are for purposes of illustrating a preferred version of the invention only and not for purposes of limiting the same, the present application discloses an anchor device for securing a drainage tube to a waste receptacle having a peripheral rim. Generally, the anchor device is configured to collapse or clinch onto the peripheral rim while directional tension or pull is applied to the drainage tube, thereby securing the drainage tube nozzle end to the waster receptacle.

Referring generally to FIG. 1-FIG. 7, a version of the anchor device 100 is described for use with a waste receptacle such as a commode or flush toilet 50 generally having a bowl 52 and a peripheral rim 54 extending about the upper perimeter of the bowl 52. Ideally, the anchor device 100 is sized to couple with the rim 54 of a flush toilet 50 of standard manufacture that disposes waste matter by using water to flush it through a drainpipe to another location for disposal, thus maintaining a separation between humans and waste matter. Typical flush toilets 50 provide a tank for holding flush water and a ceramic bowl 52 for containing water which is connected to a hollow drain pipe having a shaped bend forming a trap. Further, typical toilets 50 provide a seat overlying the bowl 52 peripheral rim 54 and spaced apart therefrom by a predetermined gap. The gap is typically maintained by a plurality of rubber bumpers on the underside of the seat. The flush toilet 50 is therefore ideal for receiving and removing matter and contaminants from a drainage tube 60 throughout the dialysis process.

Figures 4, 5:
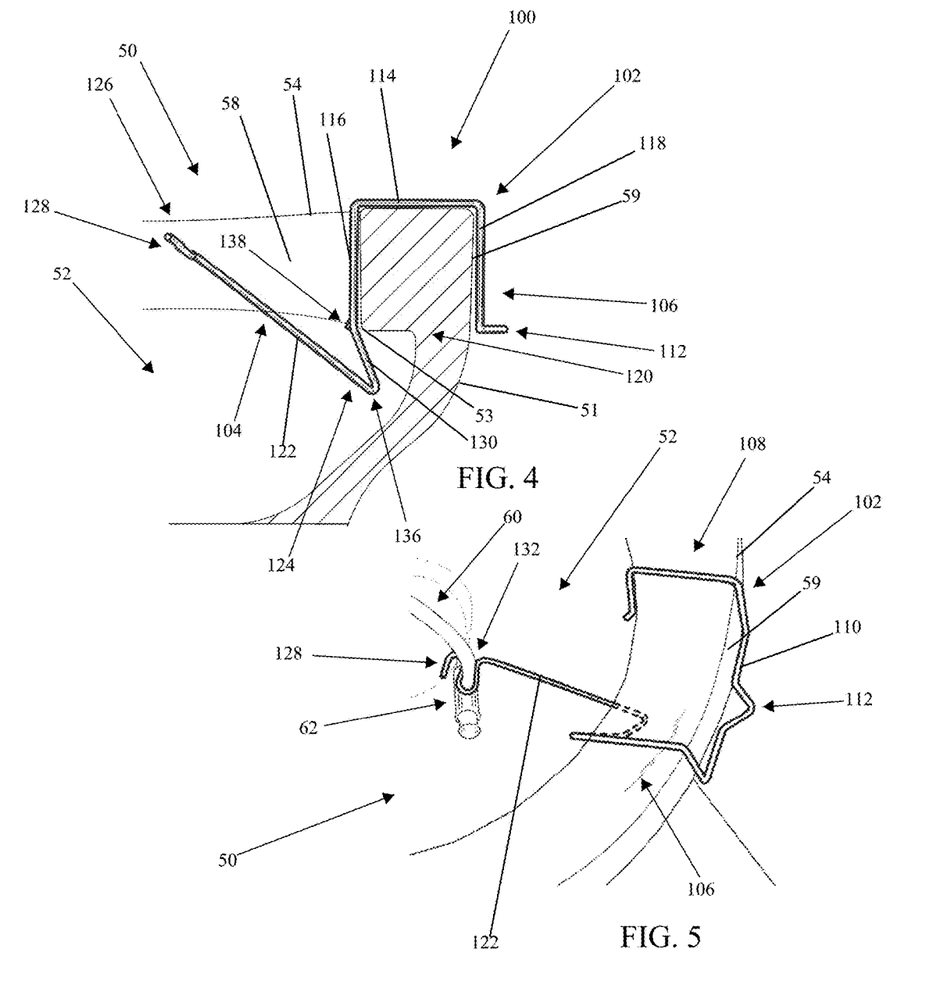
FIG. 4 is a cross-sectional view of a toilet rim showing the anchor device as shown in FIG. 1 attached thereto.
FIG. 5 is a top perspective view of the anchor as shown in FIG. 1 while operably attached to the rim of a toilet.
Figure 6:
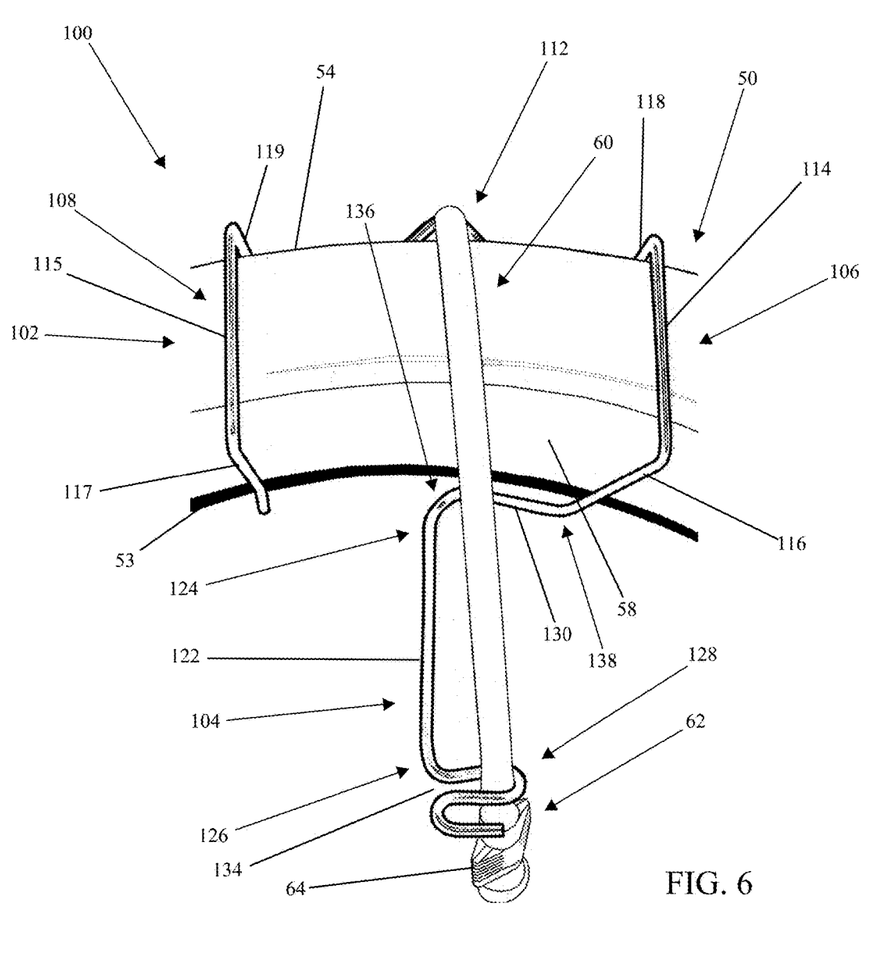
FIG. 6 is a top view of the anchor as shown in FIG. 1 while operably attached to the rim of a toilet.
Figure 7:
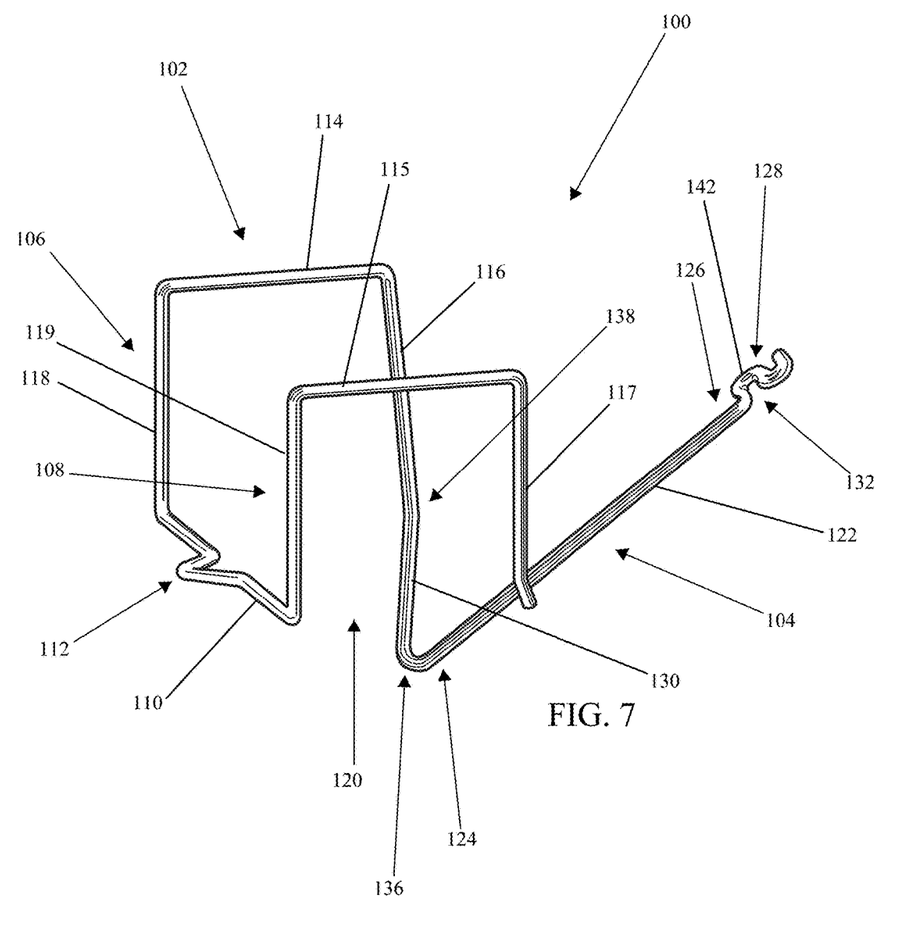
FIG. 7 is a right-side perspective view of the version shown in FIG. 1.

Typically, as shown in FIG. 4-FIG. 6, the peripheral rim 54 includes a top surface 56 having a predetermined width, an interior surface 58 having a predetermined depth terminating at a lower edge 53, and an exterior surface 59 which is typically integral with the exterior surface 51 of the bowl 52.

It is noted that the anchor device 100 may also be used with a variety of other waste receptacles which provide an upper peripheral rim such as a sink, wash basin, bowl, bathtub or even a shower providing a rim or door for attachment purposes.

Figure 2:
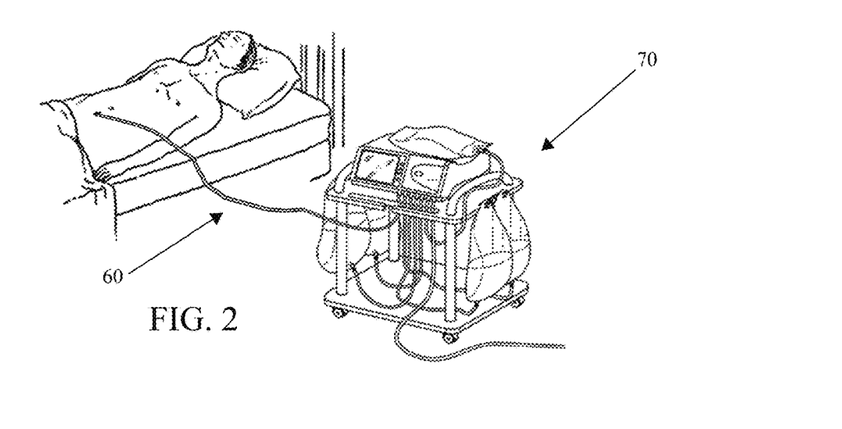
FIG. 2 is an illustrative perspective view of a peritoneal dialysis machine and patient undergoing dialysis treatment.
Figure 3:
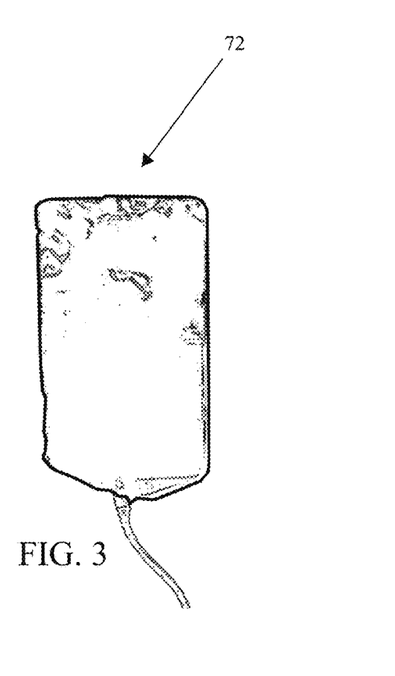
FIG. 3 is an illustrative view of a peritoneal dialysis collection bag.

As previously discussed, automated peritoneal dialysis is performed using a machine 70 (FIG. 2) that fills the peritoneal cavity with fresh dialysis solution, also called PD fluid or PD solution which is contained in a bag, and after a specified dwell time, drains the solution with waste out of the patient's body and then fills the peritoneal cavity with new dialysis solution. When the waste solution is drained from the patient, it is either drained into a bag 72 (FIG. 3) or emptied directly into a waste receptacle such as by way of the drainage tube 60 leading from the patient to a waste receptacle, or for example purposes to the flush toilet 50 as illustrated in FIG. 2. As previously discussed, often, the drainage tube 60 discharge nozzle end 62 is haphazardly and loosely attached to the waste receptacle 50 by way of an adhesive tape or other configuration.

Typically, the drainage tube 60 is a plastic medical grade tubing having a gauge of 0.25 inches and a length of 12 ft-24 ft. The drainage tube 60 terminates at the discharge nozzle end 62 and may include a valve 64 (See FIG. 6).

With reference to FIG. 1-FIG. 16, a first version of the application is shown in accordance with the general principles and components of the anchor device 100 for securing a drainage tube 60 to a waste receptacle 50 having a peripheral rim 54. As shown, the anchor device 100 generally comprises an attachment rim assembly 102 positionable for supporting the device 100 to the peripheral rim 54 of the toilet 50 and a suspension arm assembly 104 operably supported by the attachment rim assembly 102 for suspending the discharge nozzle end 62 of the drainage tube 60 towards the center interior of the bowl 52.

In a version of the application, the attachment rim assembly 102 generally comprises a first side frame structure or cradle 106 and a second side frame structure or cradle 108 laterally positioned apart and shaped to clamp over the cross-sectional profile (FIG. 4) of a segment of the peripheral rim 54. In the illustrated version of the application, a retaining bar 110 rigidly and laterally extends between and connects to the exterior side of the first and second side cradles 106, 108 together defining a distance therebetween in order to provide a working structure of the attachment rim assembly 102. Preferably, the retaining bar 110 is operably positioned below the top surface 56 of the peripheral rim 54 while attached and configured to simultaneously embraces a length or segment of the drainage tube 60 between the exterior surface 59 of the peripheral rim 54 and the retaining bar 110.

In the illustrated version, the retaining bar 110 further comprises a shaped channel guide 112 which is centrally positioned along the retaining bar 110 and generally equidistant from the first and second side cradles 106, 108. In the illustrated version, the shaped channel guide 112 is formed by an integral segment of the retaining bar 110 which is curved outward from the exterior surface 59 of the peripheral rim 54, therefore providing adequate space for the drainage tube 60 to be laced between the retaining bar 110 and the exterior surface 59 within the formed channel guide 112. The channel guide 112 serves to centrally balance and maintain the drainage tube 60 towards the center of the anchor device 100 while not restricting the flow of waste material through the drainage tube 60. Moreover, the channel guide 112 performs the function of maintaining the alignment of the drainage tube 60 when a directional pull is applied thereto.

In a preferred version, at least one of the first side cradle 106 and the second side cradle 108 comprise a top member 114, 115 which extends the top surface 56 of the peripheral rim 54, an interior member 116, 117 which extends downward adjacent to the interior surface 58 of the peripheral rim 54, and an exterior member 118, 119 which extends downward adjacent to the exterior surface 59 of the peripheral rim 54. The combination of the top members 114, 115, interior member 116, 117, and the exterior member 118, 119 form a generally rectangular profile with an open bottom which provides a form-fitting gap 120 for positioning and clamping over the cross-sectional profile of the peripheral rim 54 in a secure, rigid manner (See specifically FIG. 4).

In a version of the application, the suspension arm assembly 104 assists with supporting the discharge nozzle end 62 of the drainage tube 60 away from the rim 54 towards the center interior of the bowl 52 or other receptacle—after the tube 60 has been laced within the channel guide 112 of the retaining bar 110 as described in detail above. In the illustrated version, the suspension arm assembly 104 generally comprises a suspension arm 122 having a proximal end 124 and a distal end 126, and a tube receiver 128 positioned at the distal end 126 of the suspension arm 122.

The suspension arm 122 is operably attached to the attachment rim assembly 102 which ideally extends at an upward angle from below the elevation of the lower edge 53 and retaining bar 110 towards the center of the bowl 52 and terminating at the tube receiver 128. Ideally, in more detail, the proximal end 124 is operably positioned below the elevation of the lower edge 53 and the retaining bar 110 and is centrally positioned approximately equidistant between the first side cradle 106 and the second side cradle 108.

Now referring to FIG. 4 and FIG. 5, in a detailed version of the application, the suspension arm assembly 104 may further comprise a securing member 130 which operably attaches the attachment rim assembly 102 with the proximal end 124 of the suspension arm 122 between a first joint 136 and a second joint 138. The securing member 130 operably positions the proximal end 124 of the suspension arm 122 below the elevation of the retaining bar 110 and under the peripheral rim 54 extending towards the opposing exterior side and retaining bar 110, which facilitates securing the attachment rim assembly 102 to the peripheral rim 54 by clinching onto and under the rim 54 of the toilet 50.

Figure 1:
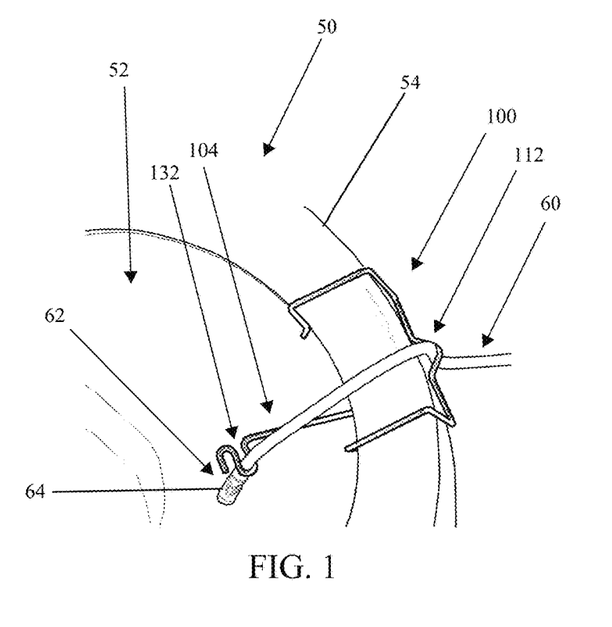
FIG. 1 is a perspective view of a version of the medical drainage tube anchor while operably attached to the rim of a toilet and supporting the nozzle end of a drainage tube towards the center of the toilet.

In a version of the application and with specific reference to FIG. 1, FIG. 5 and FIG. 6, the tube receiver 128 is generally operably configured to receive and secure the drainage tube 60 near the discharge nozzle end 62. In the illustrated version, the tube receiver 128 comprises a laterally extending channel 132 having an opening 134 having a width ideally less than the gauge of the drainage tube 60. The channel 132 is adapted to receive and retain the drainage tube 60 near the discharge nozzle end 62 without inhibiting drainage flow of the waste material from the drainage tube 60 to the waste receptacle or bowl 52. Preferably, the channel 132 is configured to direct and position the discharge nozzle end 62 of the drainage tube 60 downward towards the center interior of the bowl 52 or waste receptacle. Ideally, the channel 132 is formed by a unitary segment or length of wire which is looped back on itself providing an opening 134 having a smaller width than the channel 132 formed within the loop.

In the detailed version as illustrated by FIG. 4 and FIG. 5, the securing member 130 is rigidly connected and integral with the first side cradle 106 interior member 116. The interior member 116 extends downward and at an angle towards the center of the anchor device 100 adjacent the interior surface 58 of the peripheral rim 54 terminating and forming the second joint 138 with the inward extending securing member 130. The joint 138 forming near the height and elevation of the opposing retaining bar 110 and ideally at the lower edge 53 of the interior surface 58 of the peripheral rim 54. Operably speaking, the first and second joints 136, 138 provide a pivoting spring-like action between the attachment rim assembly 102 and the suspension arm assembly 104. Thus, when the tube receiver 128 is under duress by way of directional tension applied to the drainage tube 60, the anchor device 100 tends to collapse upon itself, further clinching to the peripheral rim 54 of the toilet 50, securing the drainage tube thereto. Moreover, the spring-like qualities of the anchor device 100 allow it to return to its original form even after tension from the drainage tube 60 causes the anchor device 100 to collapse upon itself.

Moreover, Preferably, the opening 134 of the channel 132 laterally opens away from the first side cradle 106, the first and second joints 136, 138, and the suspension arm 122. Thus, while the drainage tube 60 causes duress on the anchor device 100 by way of a directional pull, the spring-like qualities cause the tube receiver 128 and attached discharge nozzle end 62 to move towards the first side cradle 106 and towards the rim 54—and in combination with the retaining bar 110 channel guide 112 forces the discharge nozzle end 62 towards the opposing closed side 142 of the tube receiver 128, thereby locking the drainage tube 60 into the tube receiver 128.

Figure 8:
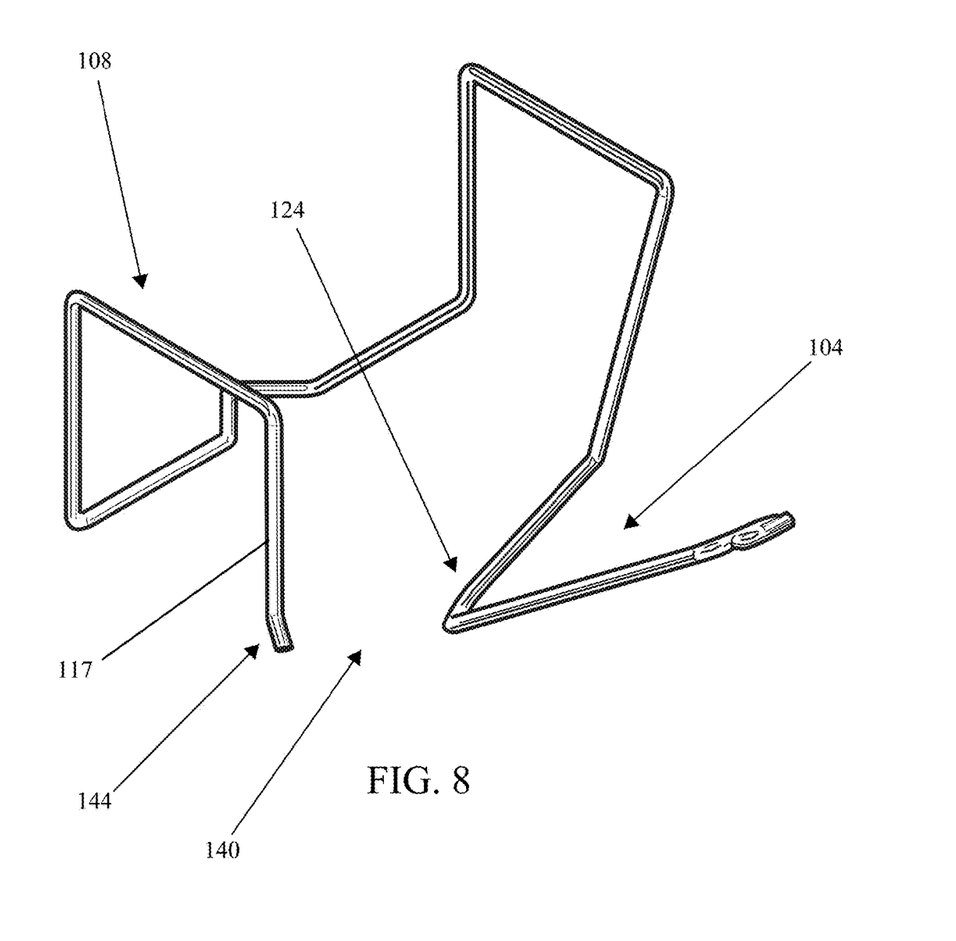
FIG. 8 is a rear perspective view of the version shown in FIG. 1.
Figure 9:
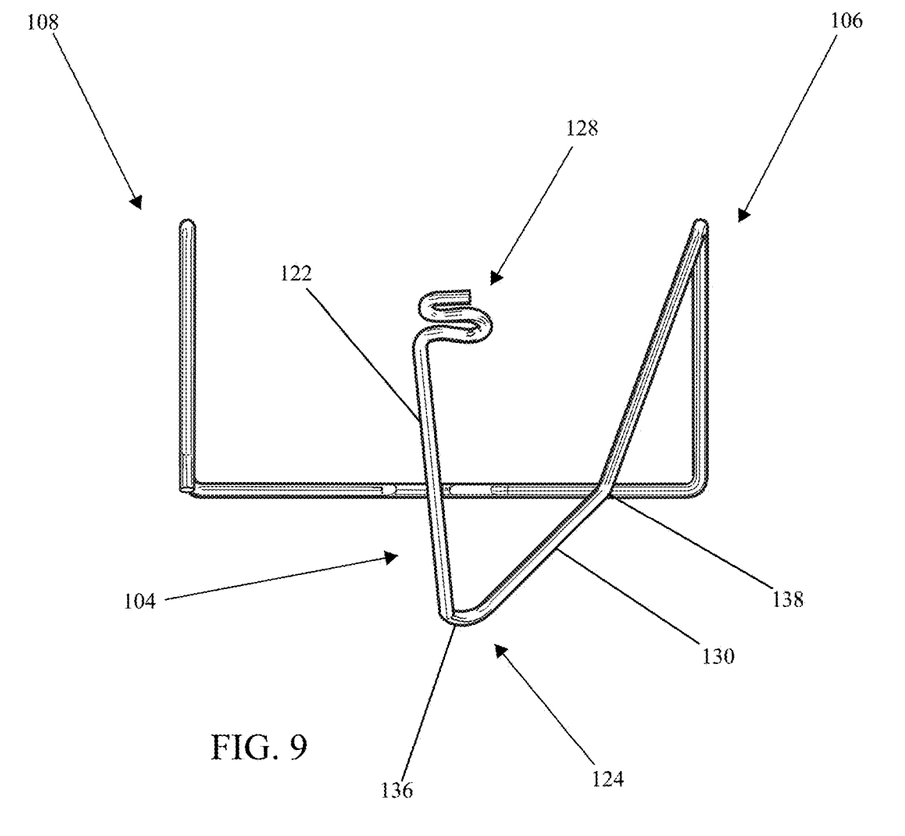
FIG. 9 is a rear elevation view of the version shown in FIG. 1.
Figure 10:
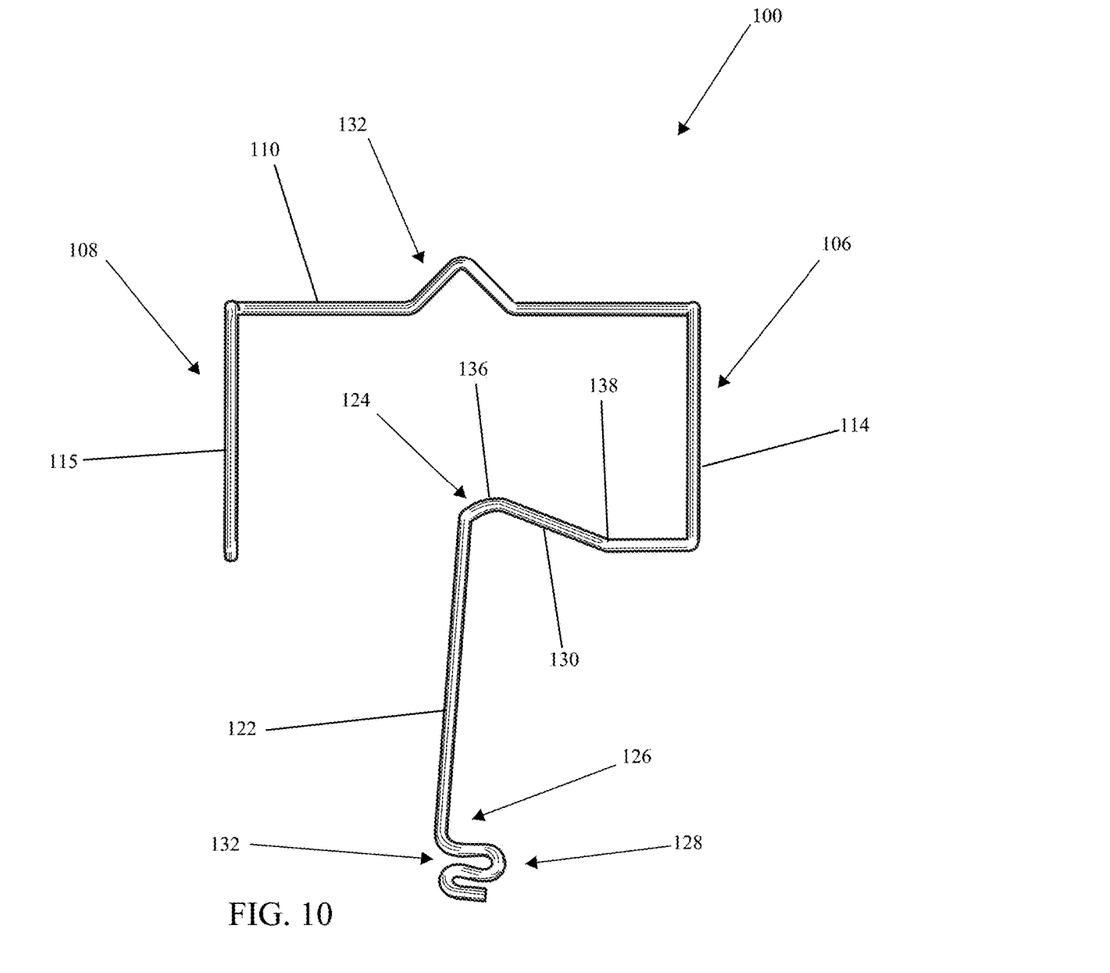
FIG. 10 is a top plan view of the version shown in FIG. 1.
Figure 11:
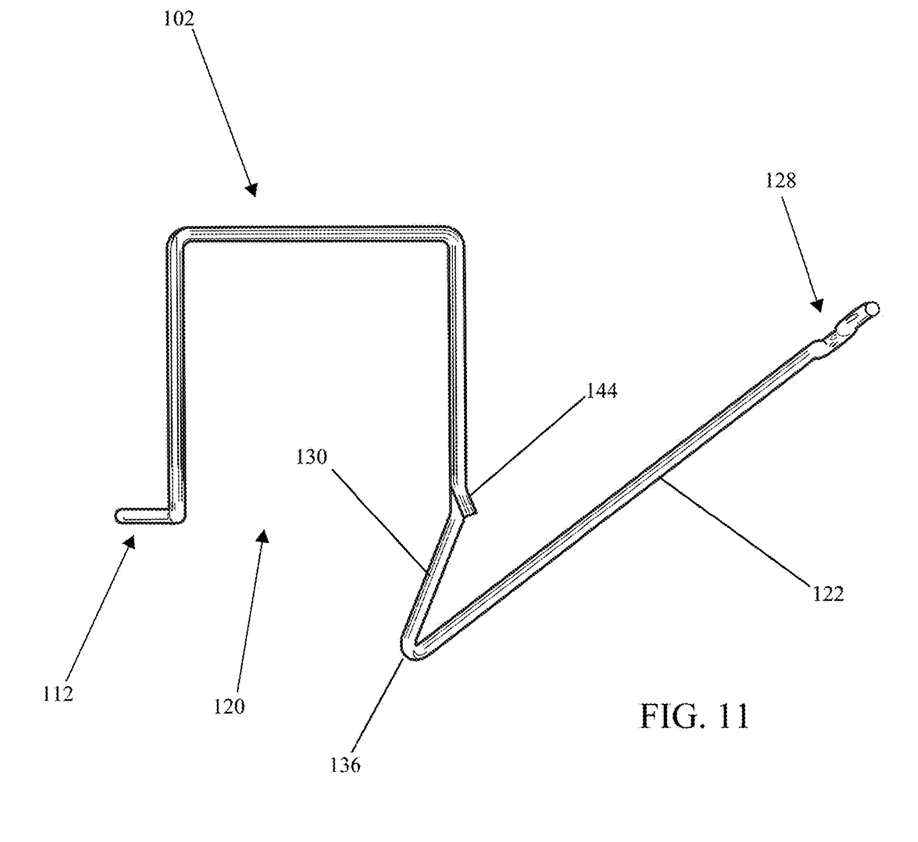
FIG. 11 is a right-side elevation view of the version shown in FIG. 1.

Referring to FIG. 8, the anchor device 100 may further comprise a gap 140 formed between the suspension arm assembly 104 proximal end 124 and the second side cradle 108 interior member 117. The gap 140 provides an opening which allows the drainage tube 60 to be easily attached to the tube receiver 128 and then aligned within the channel guide 112 of the retaining bar 110 prior to attachment of the anchor device 100 to the peripheral rim 54.

Further, the second side cradle 108 interior member 117 may further terminate with a member 144 that bends towards the interior of the bowl 52 and away from the peripheral rim 54. When directional tension of the drainage tube 60 is applied to the channel guide 112, the drainage tube 60 tends to cause lift on the anchor device 100, causing the attachment rim assembly 102 to rotate about the peripheral rim 54. The member 144 allows the attachment rim assembly 102 to rotate without causing damage to the peripheral rim 54 interior surface 58 and simultaneously allowing the first joint 136 and proximal end 124 of the suspension arm 122 to rotate further under the peripheral rim.

Referring now to FIG. 1-FIG. 11, the operation of the anchor device 100 will now be described in detail. Before the attachment of the anchor device 100 (FIG. 7), the receptacle or toilet 50 is prepared for attachment by removing any objects which are obstructing the rim such as a toilet seat and by cleaning surfaces that the anchor device 100 will contact such as the rim 54 and exterior surface 59 of the receptacle or toilet 50. Thereafter, the discharge nozzle end 62 is positioned and connected within the tapered channel 132 of the tube receiver 128 by way of the opening 134. The discharge nozzle end 62 is positioned to operably discharge the waste matter towards the center interior of the bowl 52. After that, the drainage tube 60 is woven within the gap 140, and under and within the channel guide 112 before positioning the anchor device 100 onto the peripheral rim 54. Once the drainage tube 60 is in place, the anchor device 100 attachment rim assembly 102 is coupled with the peripheral rim 54 by placing the attachment rim assembly 102 open bottom 120 over and clamping onto the cross-sectional profile of the peripheral rim 54 (See FIG. 4). Any slack that exists between the tube receiver 128 and the retaining bar 110 is removed, thus providing a slight tension between the attachment rim assembly 102 and the suspension arm assembly 104. Therefore, once connected, if the drainage tube 60 is caused to pull away from the receptacle or toilet 50, the action of the anchor device 100 tends to collapse upon itself providing a clamping force about the peripheral rim 54 of the toilet 50.

Preferably, the construction of the anchor device 100 is formed by a singular unitary length of wire having a constant gauge in order to reduce the cost of manufacturing each unit. The wire may be made of various metals, preferably of a 304-quality stainless steel with spring temper or similar metal. The 304-quality stainless steel is preferable because it does not degrade where other types do. As an alternative, 302-quality can be utilized, particularly if polished. Ideally, the gauge of the wire is between 0.75-0.105 inches, preferably 0.105 inches. Construction of the anchor device may be manufactured by way of a custom wire forming machine for purposes of efficiency.

The invention does not require that all the advantageous features and all the advantages need to be incorporated into every version of the invention.

Although preferred embodiments of the invention have been described in considerable detail, other versions and embodiments of the invention are certainly possible. Therefore, the present invention should not be limited to the described embodiments herein.

All features disclosed in this specification including any claims, abstract, and drawings may be replaced by alternative features serving the same, equivalent or similar purpose unless expressly stated otherwise.

What is claimed:

1. An anchor device for securing a drainage tube having a discharge nozzle end to a waste receptacle having a peripheral rim, the peripheral rim having a top surface of a predetermined width, an interior surface of a predetermined depth terminating at a lower edge, and an exterior surface, the anchor device comprising:
   a) an attachment rim assembly positionable for supporting the anchor device to the rim, comprising:
      i) a first side frame structure configured to couple with the rim;
      ii) a second side frame structure configured to couple with the rim;
      iii) a retaining bar laterally extending between and connecting the first and second side frame structures, the retaining bar is configured to be positioned below the top surface of the rim, and configured to retain a segment of the drainage tube between the waste receptacle and the retaining bar; and
   b) a suspension arm for suspending the discharge nozzle end of the drainage tube towards a center interior of the waste receptacle, the suspension arm having a proximal end, a distal end, and a tube receiver positioned at the distal end, the suspension arm is operably attached to the attachment rim assembly, wherein the proximal end is operably positioned below an elevation of the lower edge, and wherein the tube receiver is operably configured to receive and secure the drainage tube near the discharge nozzle end.

2. The anchor device of claim 1, wherein at least one of the first side frame structure and the second side frame structure comprise a top member extending the width of the top surface, an interior member extending downward adjacent the interior surface of the rim, and an exterior member extending downward adjacent the exterior surface of the rim, the top member, interior member, and the exterior member forming a generally rectangular profile with an open bottom for clamping over a cross-sectional profile of the rim of the waste receptacle.

3. The anchor device of claim 1, further comprising a securing member operably connecting the proximal end of the suspension arm with the attachment rim assembly and positioning the proximal end of the suspension arm below and under the rim of the waste receptacle.

4. The anchor device of claim 1, further comprising a securing member operably attached to the attachment rim assembly and extending below and under the rim of the waste receptacle.

5. The anchor device of claim 1, wherein the tube receiver comprises a laterally extending tapered channel which is adapted to receive and retain the drainage tube near the discharge nozzle end without inhibiting drainage flow of waste material from the drainage tube.

6. The anchor device of claim 5, wherein the channel is configured to direct and position the discharge nozzle end downward towards the center interior of the waste receptacle.

7. The anchor device of claim 1, wherein the proximal end of the suspension arm is positioned below the elevation of the retaining bar.

8. The anchor device of claim 1, wherein the retaining bar further comprises a channel guide which is configured to retain the segment of the drainage tube between the waste receptacle and the retaining bar.

9. The anchor device of claim 1, wherein the device is formed by a singular unitary length of wire.

10. An anchor device for securing a drainage tube having a discharge nozzle end to a waste receptacle having a peripheral rim, the peripheral rim having a top surface of a predetermined width, an interior surface of a predetermined depth terminating at a lower edge, and an exterior surface, the anchor device comprising:
  a) an attachment rim assembly positionable for supporting the anchor device to the rim, comprising:
    i) a first side cradle configured to couple with the rim;
    ii) a second side cradle configured to couple with the rim;
    iii) a retaining bar extending between and connecting the first and second side cradles, the retaining bar is configured to be positioned below the top surface of the rim, and configured to retain a length of the drainage tube between the waste receptacle and the retaining bar;
  b) a suspension arm for suspending the discharge nozzle end of the drainage tube towards the center interior of the waste receptacle, the suspension arm having a proximal end, a distal end, and a tube receiver positioned at the distal end, the suspension arm is operably attached to the attachment rim assembly, the proximal end is operably positioned below the elevation of the lower edge and the retaining bar and approximately equidistant between the first side cradle and the second side cradle, and wherein the tube receiver is operably configured to receive and secure the drainage tube near the discharge nozzle end; and
  c) a securing member operably connecting the proximal end of the suspension arm with attachment rim assembly and positioning the proximal end of the suspension arm below and under the rim of the waste receptacle towards the retaining bar.

11. The anchor device of claim 10, wherein at least one of the first side cradle and the second side cradle comprise a top member extending the width of the top surface, an interior member extending downward adjacent the interior surface of the rim, and an exterior member extending downward adjacent the exterior surface of the rim, the top member, interior member, and the exterior member forming a generally rectangular profile with an open bottom for clamping over a cross-sectional profile of the rim of the waste receptacle.

12. The anchor device of claim 10, wherein the tube receiver comprises a laterally extending tapered channel which is adapted to receive and retain the drainage tube near the discharge nozzle end without inhibiting drainage flow of waste material from the drainage tube.

13. The anchor device of claim 12, wherein the channel is configured to direct and position the discharge nozzle end downward towards the center interior of the waste receptacle.

14. The anchor device of claim 10, wherein the retaining bar further comprises a channel guide which is configured to retain a segment of the drainage tube between the waste receptacle and the retaining bar.

15. The anchor device of claim 10, wherein the device is formed by a singular unitary length of wire.

16. An anchor device for securing a drainage tube having a discharge nozzle end to a waste receptacle having a peripheral rim, the peripheral rim having a top surface of a predetermined width, an interior surface of a predetermined depth terminating at a lower edge, and an exterior surface, the anchor device comprising:
  a) an attachment rim assembly positionable for supporting the anchor device to the rim, comprising:
    i) a first side cradle configured to couple with the rim;
    ii) a second side cradle configured to couple with the rim; and
    iii) a retaining bar extending between and connecting the first and second side cradles, the retaining bar is configured to be positioned below the top surface of the rim, and configured to retain a segment of the drainage tube between the waste receptacle and the retaining bar;
  b) a suspension arm for suspending the discharge nozzle end of the drainage tube towards a center interior of the waste receptacle, the suspension arm having a proximal end, a distal end, and a tube receiver positioned at the distal end, the suspension arm is operably attached to the attachment rim assembly, the proximal end is operably positioned below an elevation of the lower edge and the retaining bar and approximately equidistant between the first side cradle and the second side cradle, and wherein the tube receiver is operably configured to receive and secure the drainage tube near the discharge nozzle end; and
  c) a securing member operably connecting the proximal end of the suspension arm with attachment rim assembly and positioning the proximal end of the suspension arm below and under the rim of the waste receptacle towards an opposing exterior side;
  d) wherein at least one of the first side frame cradle and the second side cradle comprise a top member extending the width of the top surface, an interior member extending downward adjacent the interior surface of the rim, and an exterior member extending downward adjacent the exterior surface of the rim, the top member, interior member, and the exterior member forming a generally rectangular profile with an open bottom for clamping over a cross-sectional profile of the rim of the waste receptacle.

17. The device of claim 16, wherein the tube receiver comprises a laterally extending tapered channel which is adapted to receive and retain the drainage tube near the discharge nozzle end without inhibiting drainage flow of waste material from the tube.

18. The device of claim 17, wherein the channel is configured to direct and position the discharge nozzle end of the drainage tube downward towards a center interior of the waste receptacle.

19. The device of claim 16, wherein the retaining bar further comprises a channel guide which is configured to centrally retain the segment of the drainage tube between the waste receptacle and the retaining bar.

20. The device of claim 16, wherein the device is formed by a singular unitary length of wire.

* * * * *